United States Patent
Cho et al.

(10) Patent No.: US 10,282,519 B2
(45) Date of Patent: May 7, 2019

(54) METHOD AND APPARATUS FOR PROVIDING NURSING SERVICE

(71) Applicant: LG CNS CO., LTD., Seoul (KR)

(72) Inventors: Chun Rae Cho, Seoul (KR); Jeong Pyo Kim, Seoul (KR); Sung Yong Park, Seoul (KR); Soon Gi Yoon, Seoul (KR); Kwan Pyo Lee, Seoul (KR); Moon Ho Ha, Seoul (KR); Sung Ho Kim, Seoul (KR)

(73) Assignee: LG CNS CO., LTD., Seoul (KR)

( * ) Notice: Subject to any disclaimer, the term of this patent is extended or adjusted under 35 U.S.C. 154(b) by 1038 days.

(21) Appl. No.: 14/557,279

(22) Filed: Dec. 1, 2014

(65) Prior Publication Data

US 2016/0154943 A1    Jun. 2, 2016

(51) Int. Cl.
*G06F 19/00* (2018.01)
*G16H 10/60* (2018.01)

(52) U.S. Cl.
CPC ......... *G06F 19/3418* (2013.01); *G16H 10/60* (2018.01)

(58) Field of Classification Search
CPC .... G06Q 50/24; G06Q 50/22; G06F 19/3418; G06F 19/34; G06F 19/00; G06F 19/325; G06F 19/3481; G16H 10/60; G16H 50/20; G16H 50/50; G16H 40/20
See application file for complete search history.

(56) References Cited

U.S. PATENT DOCUMENTS

| | | | | |
|---|---|---|---|---|
| 7,024,369 B1* | 4/2006 | Brown | ................ | G06F 19/3481 705/2 |
| 2013/0024382 A1* | 1/2013 | Dala | ................ | G06F 19/322 705/51 |
| 2014/0088442 A1* | 3/2014 | Soykan | ................ | B01D 61/243 600/483 |
| 2015/0269329 A1* | 9/2015 | Fearon | ................ | G06F 19/327 705/2 |
| 2015/0356701 A1* | 12/2015 | Gandy | ................ | G06Q 50/22 705/2 |

FOREIGN PATENT DOCUMENTS

| | | |
|---|---|---|
| JP | 2012185644 | 9/2012 |
| KR | 101166647 | 7/2012 |
| KR | 20130113893 | 10/2013 |

OTHER PUBLICATIONS

Korean Intellectual Property Office Application No. 10-2015-0048910, Office Action dated May 1, 2017, 9 pages.

* cited by examiner

*Primary Examiner* — Maroun P Kanaan
(74) *Attorney, Agent, or Firm* — Lee, Hong, Degerman, Kang & Waimey

(57) ABSTRACT

A method performed by an apparatus for providing nursing service is provided. The method includes: receiving result information about nursing service provided to a patient from a first medical care provider terminal, extracting rule information that is pre-set with respect to the nursing service, determining whether the result information corresponds to the rule information, and transmitting the result information to a second medical care provider terminal if the result information corresponds to the rule information.

20 Claims, 7 Drawing Sheets

FIG. 4

| ABC | Care Level | Non-skilled | Status | Admission | Payor | Hospice |
|---|---|---|---|---|---|---|
| | Physician | AHMED,SHAKIL | Allergies | NKDA | | |

| | |
|---|---|
| ○ | Resident Caution |
| ○ | Vital |
| ● | Eating |
| ● | Toilet Bladder |
| ● | Toilet Bowe |
| ● | Personal Hygiene |
| ○ | Dressing |
| ● | Bed Mobility |
| ● | Transfer |
| ○ | Walk in room |
| ● | Walk in corridor |
| ● | Locomotion on unit |
| ● | Locomotion off unit |
| ○ | Bathing |
| ● | Miscellaneous |

RESULT INFORMATION

FIG. 5

| NURSING SERVICE | QUESTION INFORMATION | RULE INFORMATION |
|---|---|---|
| Eating | Meal intake Percent | When either one of "Refused" or "0" or "25" is selected |
| Toilet Bladder | Is there any abnormality in the urine? | When "Yes" is selected |
| Toilet Bowel | Did the resident have BM? | When "No" is selected for 3 days |
| Toilet Bowel | What kind of stool was it? | When "Dry/Hard" is selected |
| Bed Mobility | Did you aid resident in applying and/or removing Multi-PODUS Boot? | When "No" is selected |
| Transfer | Does the resident complain of pain with transfer? | When "Yes" is selected |
| Bathing | If skin problem identified, what part of the body? | When any one answer is selected |
| Dressing | Did you check the entire body for blister, rash/redness, discoloration, swelling or open skin areas before or after undressing? | When "No" is selected |

FIG. 6

ADL Alert List

| Unit/Hall | U-01 ▶ | ALL ▶ | | | | | Search | |
|---|---|---|---|---|---|---|---|---|
| Unit/Room/Bed | Resident | Category | Task | CNA Input Result | CNA | Date | Shift | Comment | Confirm |
| 314 | A | Transfer | Does the resident complain of pain with transfer? | YES | ABEBE, YETNAYET | 06/22/2014 | N | | ☐ |
| 405 | B | Toilet-Bowel | Did the resident have BM (Bowel Movement) | 3Days – 0 Times Occur | BARRIE, ABIBATU | 06/22/2014 | N | | ☐ |
| 102 | C | Dressing | If skin problem identified, what part of the body? | Right Arm,Left Arm, SELECTED | YOUNG, MARVEL | 06/21/2014 | D | | ☐ |
| 308 | D | Eating | Record meal intake in percent | Refused | YOUNG, MARVEL | 06/21/2014 | D | | ☐ |
| 314 | A | Dressing | If skin problem identified, what part of the body? | Right Arm. SELECTED | YOUNG, MARVEL | 06/21/2014 | E | | ☐ |
| 522 | E | Dressing | If skin problem identified, what part of the body? | Right Arm. SELECTED | YOUNG, MARVEL | 06/21/2014 | E | | ☐ |
| 109 | F | Dressing | If skin problem identified, what part of the body? | Right Arm,Left Arm. SELECTED | YOUNG, MARVEL | 06/21/2014 | E | | ☐ |
| 577 | G | Eating | Record meal intake in percent | Refused | YOUNG, MARVEL | 06/21/2014 | D | | ☐ |
| 568 | H | Bathing | If skin problem identified, what part of the body? | Right Arm,Left Arm,Periarea, SELECTED | YOUNG, MARVEL | 06/21/2014 | D | | ☐ |
| 1001 | I | Dressing | If skin problem identified, what part of the body? | Right Arm,Left Arm,Right Leg. | YOUNG, MARVEL | | | | ☐ |

610 — 630 — 640 — 650 — 150

METHOD AND APPARATUS FOR PROVIDING NURSING SERVICE

FIELD OF THE INVENTION

The present invention relates to a method and apparatus for providing nursing service, and more particularly, to a method and apparatus for providing nursing service to a patient.

DESCRIPTION OF THE RELATED ART

Recently, nursing service is actively provided to patients due to an aging population. Nursing service is provided by a care giver by monitoring or assisting activities of a patient according to the patient's a physical condition. Examples of services provided to patients include nursing, therapy, bathing, dressing, meal preparation, grocery shopping, issuing prescriptions, washing clothes, accompanying the patient to a hospital, and other personal care.

After a care giver provides nursing service to a patient, the care giver or the patient has to record a result of the nursing service. Generally, this is done by the patient or the caregiver recording the result. Therefore, it is difficult to monitor a patient's condition in real-time and to systematically supervise action taken to address the patient's condition. Furthermore, it is difficult to supervise a patient's long term condition and management of long-term patients is inefficient.

SUMMARY OF THE INVENTION

Features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

In one aspect of the present invention, a method of providing nursing service is provided. The method includes receiving result information related to the nursing service that was provided to a patient from a first medical care provider terminal, obtaining pre-set rule information related to the nursing service, determining whether the result information corresponds to the rule information and transmitting the result information to a second medical care provider terminal if the result information corresponds to the rule information.

It is contemplated that the method further includes receiving patient condition information from at least the first medical care provider terminal or the second medical care provider terminal and determining a type of nursing service to be provided to the patient based on the condition information. It is contemplated that the method further includes transmitting data related to the determined type of nursing service to the first medical care provider terminal.

It is contemplated that the method further includes transmitting data that is related to a changed type of nursing service to the first medical care provider terminal. It is contemplated that the method further includes changing the rule information according to input data received from the second medical care provider terminal.

It is contemplated that the method further includes changing the rule information according to result information received previously from the first medical care provider terminal. It is contemplated that obtaining the rule information includes extracting the rule information from a memory if the nursing service corresponds to a notification target nursing service.

It is contemplated that the method further includes exchanging instruction information between the second medical care provider terminal and the first medical care provider terminal after transmitting the result information to the second medical care provider terminal. It is contemplated that the result information is input by a first medical care provider to the first medical care provider terminal while or after the first medical care provider provides the nursing service to the patient It is contemplated that the rule information is set according to response information related to an inquiry regarding the nursing service. It is contemplated that the nursing service includes eating assistance, dressing assistance, bathing assistance, transfer assistance, or bathroom assistance.

It is contemplated that transmitting the result information includes transmitting a push message, an e-mail, or a text message. It is contemplated that a computer-readable recording medium is provided that has recorded thereon a program for executing a method of providing nursing service.

In another aspect of the present invention, an apparatus for providing nursing service is provided. The apparatus includes a memory that stores at least one program and a processor that executes a method of providing nursing service according to control of the at least one program where the method includes receiving result information related to the nursing service that was provided to a patient from a first medical care provider terminal, obtaining pre-set rule information related to the nursing service, determining whether the result information corresponds to the rule information and transmitting the result information to a second medical care provider terminal if the result information corresponds to the rule information.

It is contemplated that the method further includes receiving patient condition information from at least the first medical care provider terminal or the second medical care provider terminal and determining a type of nursing service to be provided to the patient based on the condition information. It is contemplated that the method further includes transmitting data related to the determined type of nursing service to the first medical care provider terminal.

It is contemplated that the method further includes transmitting data that is related to a changed type of nursing service to the first medical care provider terminal. It is contemplated that the method further includes changing the rule information according to input data received from the second medical care provider terminal.

It is contemplated that the method further includes changing the rule information according to result information received previously from the first medical care provider terminal.

In another aspect of the present invention, an apparatus for providing nursing service is provided. The apparatus includes a communication unit configured to receive and transmit information, a memory configured to store information and a processor configured to control the communication unit to receive result information related to a nursing service that was provided to a patient from a first medical care provider terminal, obtain pre-set rule information related to the nursing service, determine whether the result information corresponds to the rule information and control the communication unit to transmit the result information to a second medical care provider terminal if the result information corresponds to the rule information.

Additional features and advantages of the invention will be set forth in the description which follows, and in part will be apparent from the description, or may be learned by practice of the invention. It is to be understood that both the foregoing general description and the following detailed description of the present invention are exemplary and explanatory and are intended to provide further explanation of the invention as claimed.

These and other embodiments will also become readily apparent to those skilled in the art from the following detailed description of the embodiments having reference to the attached figures, the invention not being limited to any particular embodiments disclosed.

BRIEF DESCRIPTION OF THE DRAWINGS

The above and other objects, features and other advantages of the present invention will be more clearly understood from the following detailed description taken in conjunction with the accompanying drawings, in which:

FIG. 4 illustrates a diagram of a user interface (UI) displayed on a screen of a first medical care provider terminal;

FIG. 5 illustrates an exemplary diagram of rule information;

FIG. 6 illustrates a diagram of a UI displayed on a screen of a second medical care provider terminal.

DESCRIPTION OF THE PREFERRED EMBODIMENTS

Figure 1:
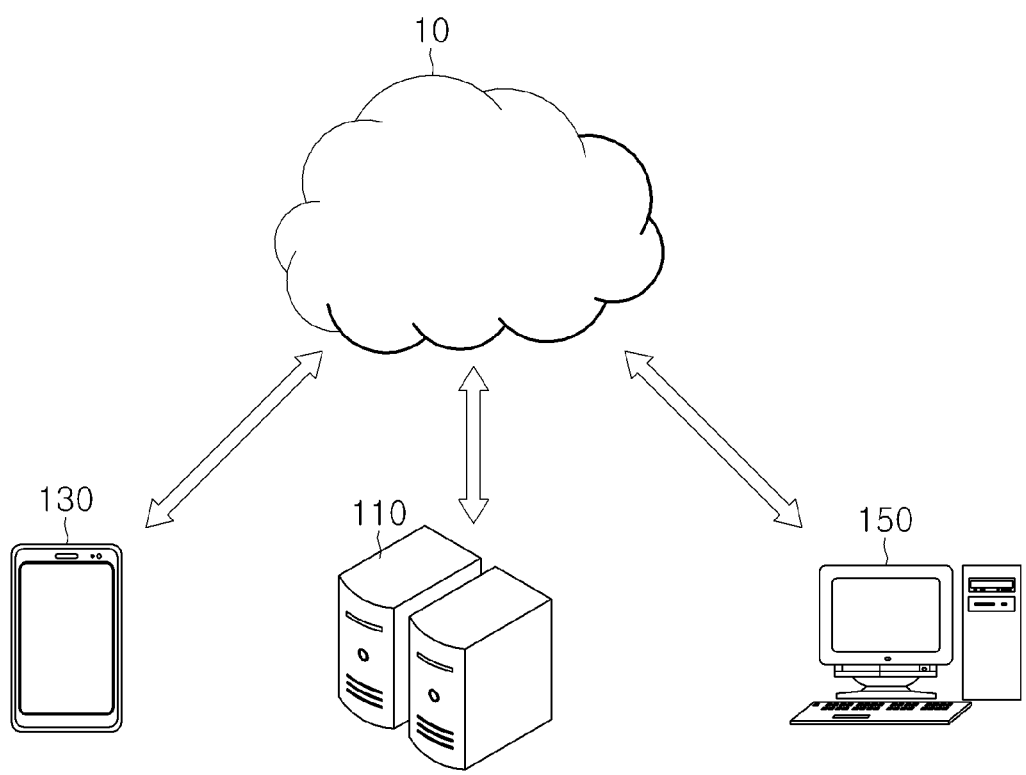
FIG. 1 illustrates a diagram of an apparatus for providing nursing service, a first medical care provider terminal, and a second medical care provider terminal, according to an embodiment of the present invention.

Exemplary embodiments of the present invention will be described in detail with reference to the accompanying drawings. While the present invention will be described in conjunction with exemplary embodiments, it is to be understood that the present invention is not limited to the exemplary embodiments. On the contrary, the present invention is intended to cover not only the exemplary embodiments, but also various alternatives, modifications and equivalents of the exemplary embodiments as well as other embodiments that may be included within the spirit and scope of the present invention as defined by the appended claims. In the drawings, like reference numerals denote like elements.

According to exemplary embodiments of the present invention, the word "unit" may refer to a software component or hardware component such as an FPGA or ASIC capable of carrying performing function or an operation. However, "unit" is not limited to hardware or software. A "unit" may be configured to reside in an addressable storage medium or to drive one or more processors. Furthermore, "unit" may refer to software components, object-oriented software components, class components, task components, processes, functions, attributes, procedures, subroutines, program code segments, drivers, firmware, microcode, circuits, data, databases, data structures, tables, arrays or variables. A function provided by a component and "unit" may be a combination of smaller components and "units" and may be combined with other components and "units" to compose large components and "units" or be further divided into "units" along with other components.

The word "patient" does not only denote a person with a disease, but also may denote a person in a hospital or a sanatorium and/or who receives nursing service due to old age or a disability. Furthermore, a "first medical care provider" denotes a medical care provider providing nursing service to a "patient" and may be a care giver, a nurse, or a nurse assistant. Moreover, a "second medical care provider" denotes a medical care provider managing a "patient's" physical condition and may be a nurse or a doctor.

FIG. 1 illustrates an apparatus 110 for providing nursing service, a first medical care provider terminal 130, and a second medical care provider terminal 150 according to an embodiment of the present invention. Referring to FIG. 1, the apparatus may be connected to the first medical care provider terminal and the second medical care provider terminal via a predetermined network. (Add to FIG. 1 with reference #)

The predetermined network may be a wired network or a wireless network. Examples of the predetermined network may include various networks, such as a local area network (LAN), a metropolitan area network (MAN), and a wide area network (WAN). The predetermined network may also include a well-known world wide web (WWW). However, examples of the predetermined network are not limited thereto and may include a well-known wireless data network, a well-known phone network, and well-known wired or wireless television networks.

The first medical care provider terminal 130 is a terminal used by a first medical care provider to provide nursing service to a patient. Examples of the first medical care provider terminal include various types of mobile terminals connectable to the apparatus 110 via the predetermined network, such as a personal digital assistant (PDA), a tablet personal computer (PC), and a laptop, as well as a smart phone as illustrated in FIG. 1.

The second medical care provider terminal 150 is a terminal used by a second medical care provider to manage a patient's physical condition. Examples of the second medical care provider terminal include various types of terminals connectable to the apparatus 110 via the predetermined network, such as a smart phone, a PDA, a tablet PC, and a laptop, as well as a desktop PC as illustrated in FIG. 1.

The apparatus 100 transmits and receives data related to the nursing service to and from the first medical care provider terminal 130 and the second medical care provider terminal 150. The apparatus may operate as a server managing data used in a hospital or a sanatorium.

Figure 2:
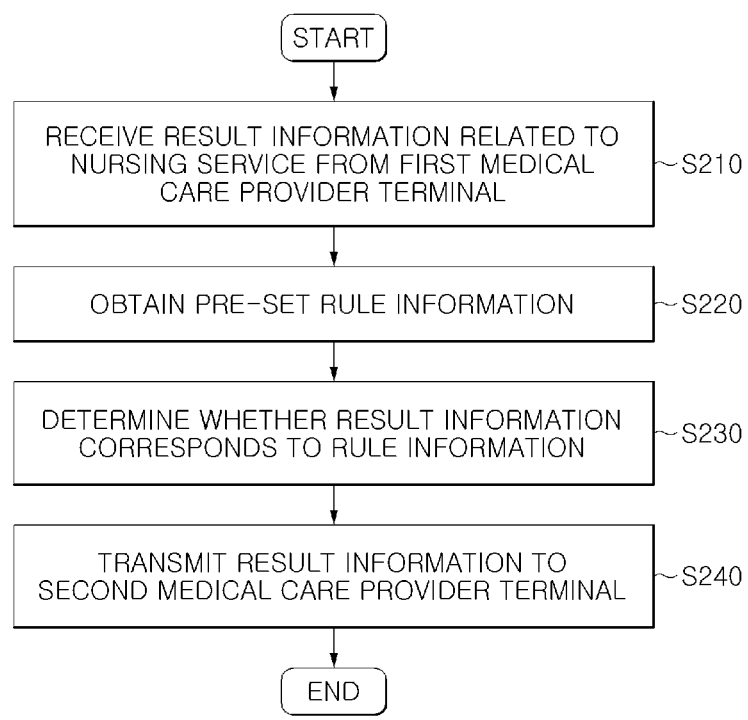
FIG. 2 illustrates a flowchart of a method for providing nursing service according to an embodiment of the present invention.

Operations of the apparatus 110, according to an embodiment of the present invention will be described with reference to FIG. 2. FIG. 2 illustrates a flowchart of a method for providing nursing service according to an embodiment of the present invention.

In operation S210, the apparatus 110 receives result information related to the nursing service provided to the patient. The information is provided from the first medical care provider terminal 130. The first medical care provider may input the result information to the first medical care provider terminal while providing or after providing nursing service to the patient. The first medical care provider terminal may transmit the result information input by the first medical care provider to the apparatus. Examples of the nursing service include eating assistance, dressing assistance, bathing assistance, transfer assistance, bathroom assistance, laundry assistance, or other personal care assistance.

In operation S220, the apparatus 110 obtains pre-set rule information related to the nursing service. The rule information is used to determine whether to transmit the result information received from the first medical care provider terminal 130 to the second medical care provider terminal 150. Result information indicating a patient's abnormal condition may be set as the rule information.

For example, if the nursing service provided is eating assistance, the rule information may indicate that the patient did not eat or that the patient left a percentage, such as 50%, of the meal. Alternatively, if the nursing service provided is transfer assistance, the rule information may indicate whether the patient complains of having pain during transfer.

In operation S230, the apparatus 110 determines whether the result information received from the first medical care provider terminal 130 corresponds to the extracted rule information. Referring to the above example, if the first medical care provider inputs result information to the first medical care provider terminal 130 that indicates the patient did not eat, the first medical care provider terminal transmits the result information to the apparatus and the apparatus determines that the result information corresponds to "patient did not eat."

In operation S240, the apparatus 110 stores the result information if the result information does not correspond to the rule information and transmits the result information to the second medical care provider terminal 150 if the result information corresponds to the rule information. The apparatus may pre-store information related to a plurality of patients as well as information related to the second medical care provider corresponding to each of the plurality of patients. When result information related to a specific patient is received from the first medical care provider terminal 130, the apparatus may transmit the result information to a terminal of the second medical care provider that corresponds to the specific patient.

Since the apparatus 110 transmits the result information to the second medical care provider terminal 150 when it is determined that the patient's physical condition is abnormal based on the result information received from the first medical care provider terminal 130, the second medical care provider may check the patient's abnormal physical condition in real-time. Furthermore, the second medical care provider may check only result information corresponding to a predetermined standard without having to check all result information input by the first medical care provider. Therefore, a workload of the second medical care provider may be reduced.

Figure 3:
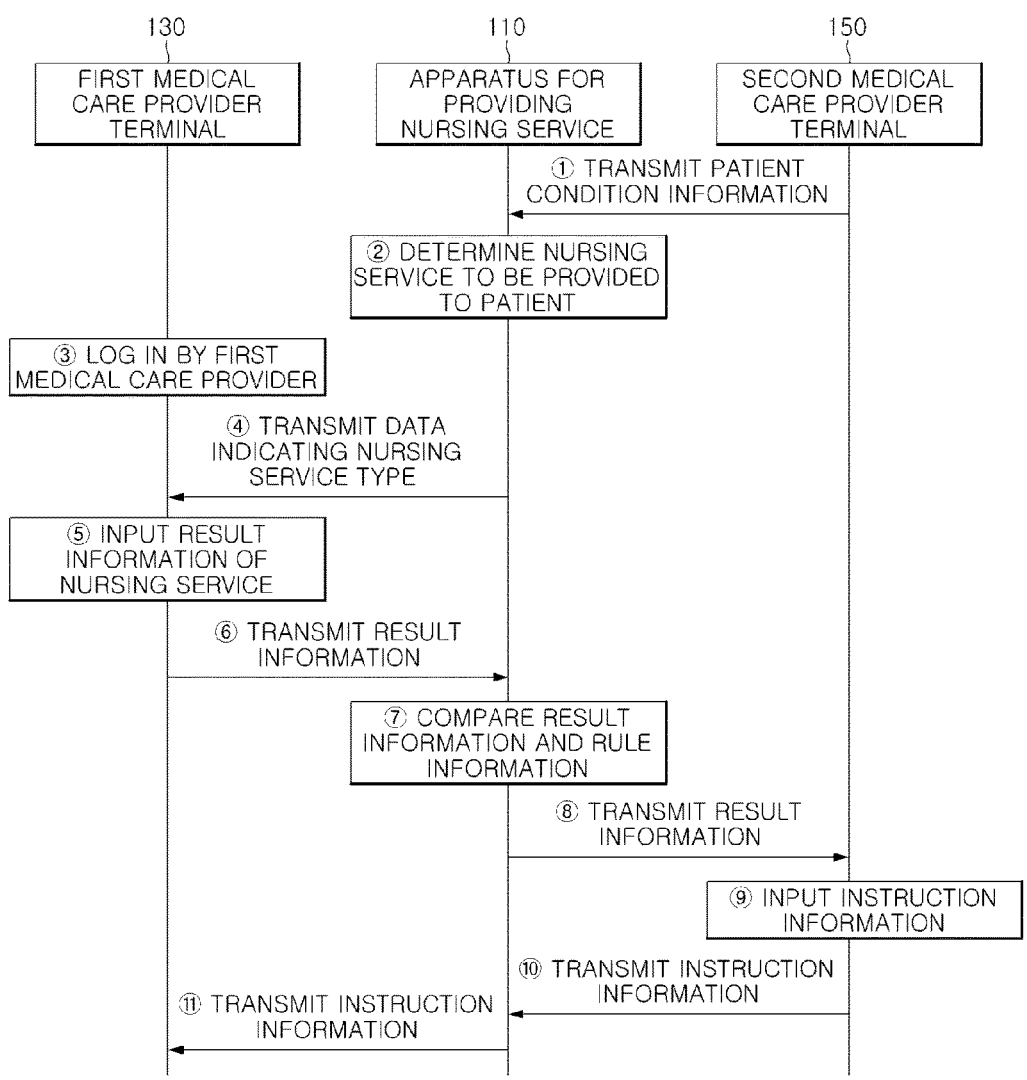
FIG. 3 illustrates a diagram for describing operations of an apparatus for providing nursing service, a first medical care provider terminal, and a second medical care provider terminal according to an embodiment of the present invention.

FIG. 3 is a diagram illustrating operations of the apparatus 110, the first medical care provider terminal 130, and the second medical care provider terminal 150 according to an embodiment of the present invention.

First, when the patient enters a hospital or a sanatorium, the second medical care provider inputs patient condition information to the second medical care provider terminal 150 and the second medical care provider terminal transmits the condition information to the apparatus 110. Alternatively, the first medical care provider may input the condition information to the first medical care provider terminal 130 and the first medical care provider terminal may transmit the condition information to the apparatus or the condition information may be directly input to the apparatus by the first or second medical care provider.

The apparatus 110 determines the type of nursing service to be provided to the patient based on the condition information. For example, if the patient's leg has a problem, the apparatus may determine transfer assistance and laundry assistance as the nursing service to be provided.

The nursing service determined by the apparatus 110 may be changed by the first and second medical care providers. The first and second medical care providers may change a type of nursing service to be provided to the patient by manipulating the first 130 and/or second 150 medical care provider terminals. Alternatively, the first and second medical care providers may change the type of nursing service by directly manipulating the apparatus.

The first medical care provider logs into the first medical care provider terminal 130 by inputting his or her identification (ID) information, such as an ID and a password, to the first medical care provider terminal. Alternatively, the first medical care provider may log into the first medical care provider terminal by inputting biometric information, such as a fingerprint, voice, or iris, to the first medical care provider terminal.

When the first medical care provider logs into the first medical care provider terminal 130, the apparatus 110 transmits data to the first medical care provider terminal 130 to indicate the type of nursing service to be provided to a patient that is assigned to the first medical care provider. If the type of nursing service is changed, the apparatus may re-transmit data to the first medical care provider terminal to indicate the changed type of nursing service.

The first medical care provider inputs the result information of the nursing service to the first medical care provider terminal 130 while or after the nursing service is provided to the patient.

The first medical care provider terminal 130 transmits the result information input by the first medical care provider to the apparatus 110.

The apparatus 110 obtains the rule information that is related to the nursing service provided to the patient and is pre-set by the first medical care provider and compares the rule information to the result information received from the first medical care provider terminal 130. The rule information stored in the apparatus may be changed by the first or second medical care provider.

For example, the first or second medical care provider may input information to the first 130 or second 150 medical care provider terminal for changing the rule information and the first or second medical care provider terminal may transmit the input information to the apparatus 110 such that the apparatus changes the rule information. Alternatively, the first or second medical care provider may change the rule information by directly manipulating the apparatus.

According to some embodiments, before extracting the rule information, the apparatus 110 may determine whether the nursing service provided to the patient by the first medical care provider is a notification target nursing service. If there are many types of nursing services to be provided to the patient and result information of all nursing services is transmitted to the second medical care provider, a workload of the second medical care provider may be too high and the apparatus may pre-determine a notification target nursing service from the many types of nursing services.

The notification target nursing service may be determined by the first and second medical care providers. If the nursing service provided to the patient by the first medical care provider is a notification target nursing service, the apparatus 110 may extract pre-set rule information related to the notification target nursing service.

If the result information received from the first medical care provider terminal 130 corresponds to the rule information, the apparatus 110 transmits the result information to the second medical care provider terminal 150. The apparatus may transmit the result information it received from the first medical care provider terminal to the second medical care provider terminal in a form of a push message, an email, or a text message.

The second medical care provider may input instruction information for the first medical care provider based on the result information received by the second medical care provider terminal 150. For example, if the second medical care provider determines that the patient is in an emergency situation based on the result information, the second medical care provider may input instruction information to the second medical care provider terminal to transfer the patient to an emergency room.

The second medical care provider terminal 150 transmits the instruction information to the apparatus 110, and (11) the apparatus transmits the instruction information to the first medical care provider terminal 130 such that the first medical care provider is able to check the instruction information.

The apparatus 110 according to an embodiment of the present invention may change the type of nursing service to be provided to the patient and the rule information based on the result information received by the first medical care provider terminal 130. Specifically, if it is determined that a specific patient's condition has improved based on result information related to nursing service provided to the specific patient, a number of type of nursing services provided to the specific patient may be reduced and rule information may be eased. For example, when transfer assistance, laundry assistance, and dressing assistance are provided to the specific patient and result information is continuously received that the specific patient did not complain of pain during transfer, the apparatus 110 may exclude laundry assistance from the services to be provided to the specific patient or may ease rule information related to the transfer assistance.

FIG. 4 illustrates a diagram of a user interface (UI) displayed on a screen of the first medical care provider terminal 130. As described previously, the first medical care provider may log into the first medical care provider terminal and receive data from the apparatus 110 indicating the type of nursing service to be provided to the patient.

As illustrated in FIG. 4, types of nursing services to be provided to the patient are displayed on a first region 410 of the screen of the first medical care provider terminal 130. The first medical care provider may select one of the types of nursing services displayed on the first region and input result information related to the selected type of nursing service to a second region 430.

At least one question related to the selected type of nursing service may be displayed on the second region 430 of the screen. The first medical care provider may input response information to the second region 430 in response to the at least one question.

According to some embodiments, pre-set response information may be provided for the at least one question. For example, if eating assistance is selected by the first medical care provider, the second region 430 of the screen may display the question "meal intake percentage?" as well as pre-set response information provided for the question, such as "refused," "50% left," "25% left," and "0% left." The first medical care provider may respond with the one of the pre-set response information displayed on the second region in order to input result information related to the eating assistance.

Furthermore, rule information related to nursing service may be pre-set based on the response information input to the question related to the nursing service or based on a number of times the response information is consecutively input. For example, if eating assistance is provided, the result information may be transmitted to the second medical care provider terminal 150 if "refused" or "25% left" is selected as the response information or if "refused" or "25% left" is continuously selected three times as the response information.

FIG. 5 illustrates an exemplary diagram of rule information. The rule information may be set based on the response information that is input in response to a question related to the nursing service.

FIG. 6 illustrates a diagram of a UI displayed on a screen of the second medical care provider terminal 150. As illustrated in FIG. 6, the screen of the second medical care provider terminal 150 may display patient information 610, a nursing service 630 provided to the patient, a question 640 regarding the nursing service, and response information 650 regarding a question. As described previously, result information displayed on the screen of the second medical care provider terminal may include result information corresponding to pre-set rule information that is received from the apparatus 110.

Figure 7:
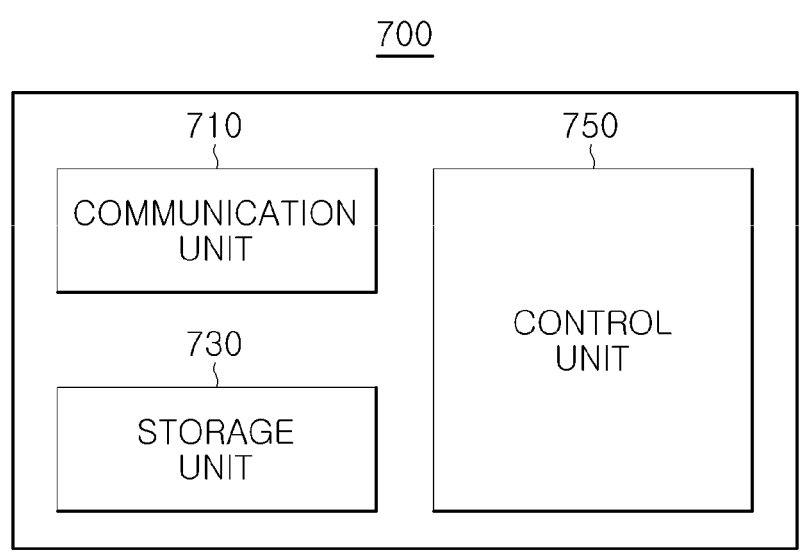
FIG. 7 illustrates a block diagram of an apparatus for providing nursing service according to another embodiment of the present invention.

FIG. 7 illustrates a block diagram of an apparatus 700 for providing nursing service according to another embodiment of the present invention. Referring to FIG. 7, the apparatus 700 may include a communication unit 710, a storage unit 730, and a control unit 750.

The communication unit 710 transmits and receives data to and from the first 130 and second 150 medical care provider terminals via a predetermined network. The storage unit 730 may include a memory storing at least one program for executing the method described previously with reference to FIGS. 2 and 3. The storage unit may also store the role information. The control unit 750 may include a processor that executes the method according to the at least one stored program. Although the control unit and communication unit are illustrated as separate in FIG. 7, the control unit and communication unit may be configured in one module.

When the communication unit 710 receives result information from the first medical care provider terminal 130 that is related to a nursing service provided to a patient, the control unit 750 extracts pre-set rule information related to the nursing service from the storage unit 730. The control unit determines whether the result information corresponds to the rule information and transmits the result information to the second medical care provider terminal 150 via the communication unit if the result information corresponds to the rule information.

When the communication unit 710 receives patient condition information from at least the first 130 or second 150 medical care provider terminal, the control unit 750 may determine a type of nursing service to be provided to the patient based on the condition information. The control unit transmits data indicating the determined type of nursing service to the first medical care provider terminal via the communication unit and re-transmits data indicating the changed type of nursing service to the first medical care provider terminal via the communication unit if the type of nursing service is changed.

The control unit 750 may also change the type of nursing service to be provided to the patient and the pre-set rule information related to the nursing service based on input data received from the first 130 or second 150 medical care provider terminal or based on result information received from the first medical care provider terminal.

Furthermore, if the communication unit 710 receives instruction information from the second medical care provider terminal 150 after the result information is transmitted to the second medical care provider terminal, the control unit 750 may transmit the instruction information to the first medical care provider terminal 130 via the communication unit.

The present invention provides a method and apparatus for providing nursing service that may enable a medical care provider to monitor a patient's condition in real-time. Furthermore, the present invention provides a method and apparatus for providing nursing service that may enable a medical care provider to quickly take action if an emergency occurs due to a patient's abnormal condition. Moreover, the present invention provides a method and apparatus for providing nursing service that may reduce a workload of a medical care provider while enabling the medical care provider to efficiently manage a patient.

The embodiments of the present invention may be provided by computer-executable programs and may be embodied within a conventional digital computer for operating the program using a computer-readable recording medium. The computer-readable recording medium may include storage media such as a magnetic storage medium (e.g., ROMs, floppy disks, hard disks, etc.), an optically readable medium (e.g., CD ROMs, DVDs, etc.), and a carrier wave (e.g., transmission via the internet).

Although preferred embodiments of the present invention have been described for illustrative purposes, those skilled in the art will appreciate that various modifications, additions and substitutions are possible, without departing from the scope and spirit of the invention as disclosed in the accompanying claims. Therefore, the disclosed embodiments of the present invention are only for illustrative purposes and should not be construed as limiting the present invention.

What is claimed is:

1. A method of providing patient care, the method comprising:
   receiving result information from a first medical care provider terminal, the result information related to non-medical care and received while the non-medical care is provided to one of a plurality of patients under care at a medical care facility;
   obtaining rule information related to the provided non-medical care while the non-medical care is provided, the rule information specific to the one of a plurality of patients and based on a previous medical condition of the one of a plurality of patients;
   comparing the received result information to the obtained rule information while the non-medical care is provided to determine if the received result information exceeds a specific threshold indicating a specific urgency of a change in the previous medical condition;
   determining at least a number of consecutive times the received result information does not exceed the specific threshold or a level of correspondence between the received result information and the obtained rule information;
   transmitting the received result information to a second medical care provider terminal while the non-medical care is provided if the received result information exceeds the specific threshold; and
   receiving care information from the second medical care provider terminal while the non-medical care is provided, the received care information indicating that future non-medical or medical care provided to the one of the plurality of patients should be changed,
   wherein future non-medical or medical care provided to the one of the plurality of patients is reduced when the determined number of consecutive times exceeds a first specific limit or the determined level is less than a second specific limit.

2. The method of claim 1, further comprising:
   transmitting the received result information to the second medical care provider terminal only when the determined number of consecutive times exceeds the first specific limit or the determined level exceeds the second specific limit; and
   determining a type of future non-medical or medical care provided to the patient based on the received care information.

3. The method of claim 2, further comprising transmitting data related to the determined type to the first medical care provider terminal.

4. The method of claim 1, further comprising changing the rule information according to the received care information.

5. The method of claim 1, further comprising changing the rule information according to result information received previously from the first medical care provider terminal.

6. The method of claim 1, wherein obtaining the rule information comprises extracting the rule information from a memory if the non-medical care corresponds to a specific nursing service.

7. The method of claim 1, further comprising exchanging instruction information between the second medical care provider terminal and the first medical care provider terminal after transmitting the received result information.

8. The method of claim 1, wherein the received result information is input by a first medical care provider to the first medical care provider terminal while the non-medical care is provided to the one of the plurality of patients by the first medical care provider.

9. The method of claim 1, wherein the rule information is set according to response information related to an inquiry regarding the non-medical care.

10. The method of claim 1, wherein transmitting the received result information comprises transmitting a push message, an e-mail, or a text message.

11. A computer-readable storage medium having recorded thereon a program for executing the method of claim 1.

12. An apparatus for providing patient care, the apparatus comprising:
   a memory that stores at least one program; and
   a processor that executes a method of providing the patient care according to control of the at least one program, the method comprising:
   receiving result information from a first medical care provider terminal, the result information related to non-medical care and received while the non-medical care is provided to one of a plurality of patients under care at a medical care facility;
   obtaining rule information related to the provided non-medical care while the non-medical care is provided, the rule information specific to the one of a plurality of patients and based on a previous medical condition of the one of a plurality of patients;

comparing the received result information to the obtained rule information while the non-medical care is provided to determine if the received result information exceeds a specific threshold indicating a specific urgency of a change in the previous medical condition;

determining at least a number of consecutive times the received result information does not exceed the specific threshold or a level of correspondence between the received result information and the rule information;

transmitting the received result information to a second medical care provider terminal while the non-medical care is provided if the received result information exceeds the specific threshold; and receiving care information from the second medical care provider terminal while the non-medical care is provided, the received care information indicating that future non-medical or medical care provided to the one of the plurality of patients should be changed, wherein future non-medical or medical care provided to the one of the plurality of patients is reduced when the determined number of consecutive times exceeds a first specific limit or the determined level is less than a second specific limit.

13. The apparatus of claim 12, wherein the method further comprises:
   transmitting the received result information to the second medical care provider terminal only when the determined number of consecutive times exceeds the first specific limit or the determined level exceeds the second specific limit; and
   determining a type of future non-medical or medical care provided to the patient based on the received care information.

14. The apparatus of claim 13, wherein the method further comprises transmitting data related to the determined type to the first medical care provider terminal.

15. The apparatus of claim 12, wherein the method further comprises changing the rule information according to the received care information.

16. The apparatus of claim 12, wherein the method further comprises changing the rule information according to result information received previously from the first medical care provider terminal.

17. An apparatus for providing patient care, the apparatus comprising:
   a communication unit configured to receive and transmit information;
   a memory configured to store information; and
   a processor configured to:
   control the communication unit to receive result information from a first medical care provider terminal, the result information related to non-medical care and received while the non-medical care is provided to one of a plurality of patients under care at a medical care facility;
   obtain rule information related to the provided non-medical care while the non-medical care is provided, the rule information specific to the one of a plurality of patients and based on a previous medical condition of the one of a plurality of patients
   compare the received result information to the obtained rule information while the non-medical care is provided to determine if the received result information exceeds a specific threshold indicating a specific urgency of a change in the previous medical condition;
   determine at least a number of consecutive times the received result information does not exceed the specific threshold or a level of correspondence between the received result information and the obtained rule information;
   control the communication unit to transmit the received result information to a second medical care provider terminal while the non-medical care is provided if the received result information exceeds the specific threshold; and
   control the communication unit to receive care information from the second medical care provider terminal while the non-medical care is provided, the received care information indicating that future non-medical or medical care provided to the one of the plurality of patients should be changed,
   wherein future non-medical or medical care provided to the one of the plurality of patients is reduced when the determined number of consecutive times exceeds a first specific limit or the determined level is less than a second specific limit.

18. The apparatus of claim 17, wherein the processor is further configured to:
   control the communication unit to transmit the received result information to the second medical care provider terminal only when the determined number of consecutive times exceeds a first specific limit or the determined level exceeds a second specific limit; and
   determine a type of future non-medical or medical care provided to the patient based on the received care information.

19. The apparatus of claim 17, wherein the processor is further configured to control the communication unit to transmit data related to the determined type to the first medical care provider terminal.

20. The apparatus of claim 17, wherein the processor is further configured to change the rule information according to the received care information.

* * * * *